US006635600B1

(12) United States Patent
Kimble et al.

(10) Patent No.: US 6,635,600 B1
(45) Date of Patent: *Oct. 21, 2003

(54) HYDROCARBON HYDROGENATION CATALYST AND PROCESS

(75) Inventors: James B. Kimble, Bartlesville, OK (US); Joseph J. Bergmeister, Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/638,782

(22) Filed: Aug. 15, 2000

Related U.S. Application Data

(62) Division of application No. 09/176,127, filed on Oct. 21, 1998, now Pat. No. 6,127,588.

(51) Int. Cl.[7] .................. B01J 23/44; B01J 23/66; B01J 27/00
(52) U.S. Cl. .................. 502/330; 502/223; 502/347
(58) Field of Search ................ 502/213, 218, 502/223, 330, 333, 347, 348

(56) References Cited

U.S. PATENT DOCUMENTS

| | | | |
|---|---|---|---|
| 3,878,260 A | 4/1975 | Kunugi et al. .......... 260/680 E |
| 3,932,548 A | 1/1976 | Rausch .................. 260/668 D |
| 3,962,285 A * | 6/1976 | Cusumano .......... 260/348.5 R |
| 3,980,585 A * | 9/1976 | Kerr et al. .......... 260/346.8 M |
| 4,113,970 A | 9/1978 | Tanabe et al. .............. 560/244 |
| 4,341,912 A | 7/1982 | Takahashi et al. .......... 585/443 |
| 4,409,410 A * | 10/1983 | Cosyns et al. ............. 585/259 |
| 4,429,155 A * | 1/1984 | Goetz et al. ................ 564/402 |
| 4,431,750 A * | 2/1984 | McGinnis et al. .......... 502/329 |
| 4,484,015 A | 11/1984 | Johnson et al. ............. 585/262 |
| 4,717,781 A | 1/1988 | Imai et al. .................. 585/441 |
| 5,057,206 A * | 10/1991 | Engel et al. ................ 208/143 |
| 5,179,057 A * | 1/1993 | Bartley ....................... 502/170 |
| 5,314,854 A * | 5/1994 | Galperin ...................... 502/66 |
| 5,362,695 A * | 11/1994 | Beck et al. ................... 502/62 |
| 5,401,705 A * | 3/1995 | Amelse ...................... 502/174 |
| 5,475,173 A | 12/1995 | Cheung et al. ............. 585/259 |
| 5,488,024 A | 1/1996 | Cheung et al. ............. 502/325 |
| 5,489,565 A | 2/1996 | Cheung et al. ............. 502/325 |
| 5,510,550 A * | 4/1996 | Cheung et al. ............. 585/259 |
| 5,516,851 A * | 5/1996 | Flick et al. .............. 525/330.2 |
| 5,583,274 A | 12/1996 | Cheung et al. ............. 585/261 |
| 5,585,318 A | 12/1996 | Johnson et al. ............. 502/330 |
| 5,587,348 A | 12/1996 | Brown et al. ............... 502/230 |
| 6,127,310 A * | 10/2000 | Brown et al. ............... 502/339 |

\* cited by examiner

*Primary Examiner*—Bekir L. Yildirim
(74) *Attorney, Agent, or Firm*—Conley Rose, P.C.; Rodney B. Carroll

(57) ABSTRACT

A supported hydrogenation catalyst composition is disclosed which comprises palladium, an inorganic support such as alumina, and a selectivity enhancer selected from the group consisting of silver, phosphorus, sulfur, and combinations of two or more thereof. Also disclosed is a selective hydrogenation process in which highly unsaturated hydrocarbons such as diolefins and/or alkynes are hydrogenated with hydrogen to less unsaturated hydrocarbons such as monoolefins.

13 Claims, No Drawings

HYDROCARBON HYDROGENATION CATALYST AND PROCESS

This application is a Division of application Ser. No. 09/176,127, now filed on Oct. 28, 1998 U.S. Pat. No. 6,127,588.

FIELD OF THE INVENTION

This invention relates to a supported noble metal catalyst composition and to a process for selectively hydrogenating a highly unsaturated hydrocarbon employing a supported noble metal catalyst composition.

BACKGROUND OF THE INVENTION

Catalysts comprising palladium and an inorganic support are known catalysts for the hydrogenation of polyenes and/or alkynes. Even though these catalysts are effective hydrogenation catalysts, they ten to produce green oil by oligomerizing alkenes, polyenes, and/or alkynes. Green oil, as used herein, refers to molecules having 6 or more carbon atoms per molecule and is undesirable in the production of an alkene because it fouls the hydrogenation catalyst which in turn deactivates the catalyst. The deactivation process can lower the activity and selectivity of the catalyst. Therefore, there is an ever present need for further improvements in the selective hydrogenation process for converting a highly unsaturated hydrocarbon to a less unsaturated hydrocarbon and to achieve enhanced selectivity to the less unsaturated hydrocarbon, or increased catalyst life, or both. Accordingly, the development of a modified supported palladium catalyst composition and its use in processes for the selective hydrogenation of highly unsaturated hydrocarbons such as diolefins (alkadienes) or alkynes to less unsaturated hydrocarbons such as monoolefins (alkenes) would be a significant contribution to the art.

SUMMARY OF THE INVENTION

It is an object of this invention to provide a palladium-containing catalyst composition which can be useful as a catalyst in the selective hydrogenation of a highly unsaturated hydrocarbon such as a diolefin and/or alkyne to a less unsaturated hydrocarbon such as a monoolefin. It is another object of this invention to employ this catalyst composition in the selective hydrogenation of highly unsaturated hydrocarbons such as diolefins or alkynes to monoolefins. An advantage of this invention is the increased or enhanced selectivity to a desired product and the decreased production of oligomers which form green oils, thereby increasing the life cycle of the catalyst. Other objects and advantages will become more apparent as the invention is more fully disclosed hereinbelow.

According to a first embodiment of this invention, a catalyst composition is provided which comprises, consists essentially of, or consists of palladium, an inorganic support material, and a selectivity enhancer which is silver, phosphorus, sulfur, or combinations of two or more thereof. The inorganic support can be a spinel, alumina, silica, titania, zirconia, an aluminosilicate, an aluminate such as zinc aluminate, magnesium aluminate, calcium aluminate, or combinations of two or more thereof.

According to a second embodiment this invention, a process which can be used for selectively hydrogenating a highly unsaturated hydrocarbon to a less unsaturated hydrocarbon is provided. The process comprises contacting a highly unsaturated hydrocarbon with hydrogen, in the presence of a catalyst composition, under a condition sufficient to effect a selective hydrogenation of the highly unsaturated hydrocarbon. The catalyst composition can be the same as the composition disclosed in the first embodiment of this invention.

DETAILED DESCRIPTION OF THE INVENTION

As used in the present invention, the term "fluid" denotes gas, liquid, or combination thereof. The term "selectivity enhancer" denotes an element or compound which enhances the selectivity to an alkene, decreases the selectivity to an alkane, or decreases the selectivity to an undesirable product such as green oils when the composition of the invention is employed as a catalyst in a selective hydrogenation process disclosed in this invention. The term "substantial" or "substantially" generally means more than trivial. A "saturated hydrocarbon" is referred to as any hydrocarbon which does not contain any carbon to carbon multiple bonds. An "unsaturated hydrocarbon" as used in this invention is a hydrocarbon having at least one double bond or triple bond between carbon atoms in the molecule. Example of saturated hydrocarbons include, but are not limited to, ethane, propane, butanes, pentanes, hexanes, octanes, decanes, naphtha, and combinations of any two or more thereof. Examples of unsaturated hydrocarbons include, but are not limited to, monoolefins such as ethylene, propylene, butenes, pentenes, hexenes, octenes, and decenes; aromatic compounds such as benzene and naphthalene; alkynes such as acetylene, propyne, and butynes; diolefins such as propadiene, butadienes, pentadienes (including isoprene), hexadienes, octadienes, and decadienes; and combinations of two or more thereof. The term "highly unsaturated hydrocarbon" refers to a hydrocarbon which contains a triple bond or two or more double bonds in a molecule. The term "less unsaturated hydrocarbon" refer to a hydrocarbon in which the triple bond in the highly unsaturated hydrocarbon is hydrogenated to a double bond or a hydrocarbon in which the number of double bonds is one less, or at least one less, than that in the highly unsaturated hydrocarbon. The term "selective hydrogenation" is referred to as a hydrogenation process which converts a highly unsaturated hydrocarbon such as an alkyne or a diolefin to a less unsaturated hydrocarbon such as a monoolefin without hydrogenating the less unsaturated hydrocarbon to a more saturated hydrocarbon or a saturated hydrocarbon such as alkane.

The composition of this invention comprises, consists essentially of, or consists of (a) palladium such as palladium metal, palladium oxide, or combinations thereof in which the palladium can be present as a "skin" distributed on the surface of an inorganic support, (b) an inorganic support selected from the group consisting of alumina, silica, titania, zirconia, aluminosilicates (clays and/or zeolites), a spinel such as zinc aluminate, zinc titanate and magnesium aluminate, and combinations of two or more thereof, (c) a selectivity enhancer selected from the group consisting of silver, silver compounds, phosphorus, sulfur, phosphorus compounds, sulfur compounds, potassium, potassium compounds, and combinations of two or more thereof, and optionally (d) a fluorine- or fluoride-containing compound. Examples of suitable selectivity enhancer compounds include, but are not limited to, silver, silver nitrate, silver chloride, potassium phosphate, sodium phosphate, ammonium phosphate, sodium sulfate, potassium sulfate, ammonium sulfate, and combinations of two or more thereof. The term "phosphate" also includes dibasic and monobasic phosphates. Examples of suitable fluorine- or fluoride-containing compounds include, but are not limited to, non-alkali metal fluorides such as ammonium fluoride, hydrogen fluoride, and ammonium hydrogen fluoride; alkali metal fluorides such as sodium fluoride, potassium fluoride rubidium fluoride, and cesium fluoride; and combinations of two or more thereof.

Generally, the composition can contain about 0.001 to about 3, preferably about 0.001 to about 2 weight % Pd; about 0.002 to about 10, preferably about 0.01 to about 5 weight % each selectivity enhancer; optionally about 0.002 to about 10, preferably about 0.01 to about 5 weight % fluorine; and the rest being inorganic support. The composition can have any suitable shape such as spherical, cylindrical, trilobal, or combinations of two or more thereof. The preferred shape is either spherical or cylindrical. The particles of this catalyst generally have a size of about 1 to about 10 mm, preferably about 2 to about 6 mm. Generally the surface area of the catalyst as measured by the BET method (Brunauer, Emmett and Teller) employing $N_2$ is 0.5 to about 200, preferably about 1 to about 100 m²/g.

The composition can be produced by any suitable means known to one skilled in the art. For example, the components (a) and (c) as well as the optional component (d) can be deposited onto and/or incorporated into the inorganic support by any suitable means. For instance, the selectivity enhancer(s) can be incorporated, such as by impregnation or spraying, into the support material before it is incorporated or impregnated with a suitable palladium compound, and preferably also with a suitable silver compound. Alternatively, at least one alkali metal compound can be incorporated, such as by impregnation or spraying, into the catalyst simultaneously with or after the impregnation with a suitable palladium compound. When silver is also present in the catalyst composition, then at least one selectivity enhancer can be incorporated between the palladium and silver impregnation steps or after the impregnation of the palladium and silver compounds. In the presently preferred catalyst preparation, a supported Pd/Ag catalyst material, more preferably $Pd/Ag/Al_2O_3$ which can be produced by the method described in U.S. Pat. Nos. 4,404,124 and 4,484,015, is impregnated with an aqueous solution of at least one catalyst modifier, followed by drying, generally at 50° C. to 150° C., and optionally calcining, preferably in air at a temperature of 300° C. to 700° C., more preferably at 350° C. to 650° C., preferably for 0.5 to 20 hours, more preferably from 1 to 10 hours.

A non-alkali metal fluoride, preferably HF, $NH_4F$, or $NH_4HF_2$ or combinations of two or more thereof, can be incorporated into the catalyst in any suitable manner. The non-alkali metal fluoride can be incorporated together with palladium and a selectivity enhancer and preferably a suitable silver compound. Preferably, the non-alkali metal fluoride can be incorporated after the impregnation of the solid inorganic support with palladium and at least one selectivity enhancer and, preferably, also a suitable silver compound. After the incorporation of Pd, any selectivity enhancer(s), fluoride and, preferably also silver into the inorganic support been completed as described above, the resultant material can be dried, generally at about 50° C. to 150° C., for about 0.01 to 10 hours, and then optionally calcined, generally at a temperature of about 300° C. to 700° C., for about 0.5 to 20 hours. Optionally, the catalyst can be reduced with hydrogen gas, preferably at 10° C. to 200° C. for about 0.1 to 20 hours, so as to reduce the oxides of palladium and silver, if present, to the corresponding metal(s).

According to the second embodiment of this invention, a selective hydrogenation process is provided. The selective hydrogenation process of this invention can comprise, consist essentially of, or consist of contacting feed which contains one or more highly unsaturated hydrocarbon(s), in the presence of hydrogen, with the catalyst composition disclosed above. Preferably the feed containing the highly unsaturated hydrocarbon(s) also comprises an unsaturated hydrocarbon(s). The highly unsaturated hydrocarbon is present as an alkyne, a polyene, such as a diolefin, or combinations of two or more thereof, as an impurity, generally at a level of about 1 mg/Kg (ppm) to about 50,000 ppm each in the feed. The unsaturated hydrocarbon(s) in the feed can be one or more alkenes.

Examples of suitable alkynes include, but are not limited to, acetylene, propyne, 1-butyne, 2-butyne, 1-pentyne, 2-pentyne, 3-methyl-1-butyne, 1-hexyne, 1-heptyne, 1-octyne, 1-nonyne, 1-decyne, and combinations of two or more thereof. The presently preferred alkynes are acetylene and propyne.

These alkynes are primarily hydrogenated to the corresponding alkenes. For example, acetylene is primarily hydrogenated to ethylene, propyne is primarily hydrogenated to propylene, and the butynes are primarily hydrogenated to the corresponding butenes (1-butene, 2-butenes).

Examples of suitable polyenes include those containing about 3 to about 12 carbon atoms per molecule. The presently preferred polyenes are diolefins. Such diolefins include, but are not limited to, propadiene, 1,2-butadiene, 1,3-butadiene, isoprene, 1,2-pentadiene, 1,3-pentadiene, 1,4-pentadiene, 1,2-hexadiene, 1,3-hexadiene, 1,4-hexadiene, 1,5-hexadiene, 2-methyl-1,2-pentadiene, 2,3-dimethyl-1,3-butadiene, heptadienes, methylhexadienes, octadienes, methylheptadienes, dimethylhexadienes, ethylhexadienes, trimethylpentadienes, methyloctadienes, dimethylheptadienes, ethyloctadienes, trimethylhexadienes, nonadienes, decadienes, undecadienes, dodecadienes, cyclopentadienes, cyclohexadienes, methylcyclopentadienes, cycloheptadienes, methylcyclohexadienes, dimethylcyclopentadienes, ethylcyclopentadienes, dicyclopentadiene, and mixtures of one or two of these diolefins. Presently preferred diolefins are propadiene, 1,3-butadiene, pentadienes (such as 1,3-pentadiene, 1,4-pentadiene, isoprene), cyclopentadienes (such as 1,3-cyclopentadiene) and dicyclopentadiene (also known as tricyclo[5.2. 1]$^{2,6}$deca-3,8-diene). These diolefins are preferably hydrogenated to their corresponding monoolefins containing the same number of carbon atoms per molecule as the diolefins. For example, propadiene is hydrogenated to propylene, 1,3-butadiene is hydrogenated to 1-butene and 2-butene, 1,3-pentadiene and 1,4-pentadiene are hydrogenated to 1-pentene and 2-pentene, isoprene is hydrogenated to methyl-1-pentenes and methyl-2-pentenes, and 1,3-cyclopentadiene is hydrogenated to cyclopentene.

The highly unsaturated hydrocarbon-containing feed for the hydrogenation process of this invention can also comprise one or more additional hydrocarbons, in particular, monoolefins, aromatic hydrocarbons, and saturated hydrocarbons. Examples of such other hydrocarbons which can be present in the feed at a level of 0.001 to 99.999 weight % include, but are not limited to, ethylene, propylene, 1-butene, 2-butene, isobutylene, 1-pentene, 2-pentene, methyl-1-butenes (such as 2-methyl-1-butene), methyl-2-butenes (such as 2-methyl-2-butene), 1-hexene, 2-hexene, 3-hexene, methyl-1-pentenes, 2,3-dimethyl-1-butene, 1-heptene, 2-heptene, 3-heptene, methyl-1-hexenes, methyl-2-hexenes, methyl-3-hexenes, dimethylpentenes, ethylpentenes, octenes, methylheptenes, dimethylhexenes, ethylhexenes, nonenes, methyloctenes, dimethylheptenes, ethylheptenes, trimethylhexenes, cyclopentene, cyclohexene, methylcyclopentene, cycloheptene, methylcyclohexene, dimethylcyclopentenes, ethylcyclopentenes, cyclooctenes, methylcycloheptenes, dimethylcyclohexenes, ethylcyclohexenes, trimethylcyclohexenes, methylcyclooctenes, dimethylcyclooctenes, ethylcylcooctenes, benzene, toluene, ethylbenzene, styrene, xylenes, methane, ethane, propane, butane, methylpropane, methylbutane, dimethylbutane, pentanes, hexanes, and the like, and combinations of two or more than two of these hydrocarbons.

Furthermore, the fluid feed can contain 0.001 to about 5 weight % hydrogen, and up to 5000 parts per million volume (ppmv) of carbon monoxide.

Also, the feed can contain small amounts, generally less than about 0.05 weight %, in particular about 0.1 to about 400 ppm S, as sulfur compounds, such as $H_2S$, carbonyl sulfide, carbon disulfide, mercaptans, organic sulfides such as dimethyl sulfide, thiophene, organic di-, tri- and tetrasulfides, and combinations of two or more thereof, as impurities.

The selective hydrogenation process of this invention is generally carried out by contacting a feed stream comprising at least one highly unsaturated hydrocarbon and molecular hydrogen with the catalyst of this invention which is generally contained in a fixed bed. Generally, about 0.1 to about 100, preferably about 0.7 to about 30, moles of hydrogen are employed for each mole of the highly unsaturated hydrocarbon present in the feed. The temperature necessary for the selective hydrogenation process of this invention depends largely upon the activity of the catalyst composition, the hydrocarbon feed composition, and the desired extent of hydrogenation. Generally, reaction temperatures in the range of from about 10° C. to about 300° C., preferably about 20° C. to about 250° C., and most preferably 30° C. to 200° C. can be used. A suitable reaction pressure generally is in the range of about 15 to about 2,000 pounds per square inch gauge (psig), preferably 50 to about 1,500 psig, and most preferably 100 to 1,000 psig. The gas hourly space velocity (GHSV) of the hydrocarbon feed can vary over a wide range. Typically, the space velocity of the feed will be in the range of about 500 to about 40,000 liters of hydrocarbon feed per liter of catalyst hour, more preferably about 1,000 to about 30,000 liters/liter catalyst hour. The hydrogenation process conditions should be such as to avoid significant hydrogenation of monoolefins, which are formed by hydrogenation of the highly unsaturated hydrocarbons being initially present in the feed, to saturated hydrocarbons such as alkanes and cycloalkanes.

If it is desired to regenerate the catalyst composition of this invention after prolonged use in a hydrogenation process, this can be accomplished by calcining the catalyst in an oxidizing atmosphere such as in air at a temperature that does not exceed about 700° C. to burn off carbonaceous and sulfur deposits. Optionally, the catalyst can be reimpregnating with selectivity enhancer(s) and heated as described above for the production of fresh catalyst composition of this invention.

The following examples are presented to further illustrate this invention and should not be construed as unduly limiting the scope of this invention.

EXAMPLE I

This example illustrates the preparation of various palladium catalysts.

Catalyst A was an $Ag/Pd/Al_2O_3$ catalyst. It was commercially available from UCI (United Catalyst Inc., Louisville, Ky.) under the production designation of G83C which contained about 0.06 weight % Ag and about 0.02 weight % Pd.

Catalyst B was a $KF/Ag/Pd/Al_2O_3$ catalyst which was produced by the process disclosed in U.S. Pat. No. 5,587,348, the description of which is incorporated herein by reference. Catalyst B contained about 0.02 weight % Pd, about 0.06 weight % Ag, and about 0.3 weight % K (as KF).

Catalyst C was a $K_3PO_4/Ag/Pd/Al_2O_3$ catalyst. It was produced by impregnating 25.03 grams of catalyst A described above with a solution containing 0.14 g potassium phosphate ($K_3PO_4$) and 6.26 g distilled water. The $K_3PO_4$-impregnated catalyst was dried at 250° C. for 16 hours (overnight) then calcined at 470° C. for 4 hours. Catalyst C contained 0.02 weight % Pd, 0.06 weight % Ag and 0.03 weight % K (as $K_3PO_4$).

Catalyst D was a $K_2HPO_4/Ag/Pd/Al_2O_3$ catalyst. It was produced by impregnating 25.04 g of catalyst A with a solution containing 0.17 g of $K_2HPO_4$ and 6.28 g of distilled water followed by drying and calcining as disclosed above for catalyst C. It contained 0.02 weight % Pd, 0.06 weight % Ag, and 0.3 weight % K (as $K_2HPO_4$).

Catalyst E was $K_2SO_4/Ag/Pd/Al_2O_3$ produced by impregnating 25.01 g of catalyst A with a solution containing 0.17 g of $K_2SO_4$ and 6.28 g of distilled water followed by drying and calcining as disclosed above for catalyst C. It contained 0.02 weight % Pd, 0.06 weight % Ag, and 0.3 weight % K (as $K_2SO_4$).

EXAMPLE II

This example illustrates the selective hydrogenation of acetylene employing catalysts described in Example I.

The gaseous hydrocarbon feed employed in the following hydrogenation tests was: 900 cc/min of a blend of 98.187 weight % ethylene, 1.085 weight % methane, 0.692 weight % acetylene, and 0.0302 weight % ethane. Hydrogen was co-fed with the hydrocarbon feed at 10 cc/min. These gases were passed into a reactor at 200 psig. The reactor was a stainless steel tube having an inner diameter of 0.5 inch (1.225 centimeters) and a length of 18 inches (45.72 centimeters); packed with 27 g of each of the catalysts produced in Example I in which each catalyst was mixed with 26 ml of 0.3 mm glass beads; and was submerged in a water bath and the feed was admitted to the reactor which had a temperature varied from 100° F. to 150° F. for obtaining desired conversions. The reactor effluent or product stream was analyzed by gas chromatography. Acetylene conversion at various hydrogen conversion is shown in Table I and ethane selectivity at various acetylene conversion is shown in Table II.

TABLE I

| | Acetylene Conversion[a] | | | | | | | | |
|---|---|---|---|---|---|---|---|---|---|
| $H_2$ Conversion (%) | 40 | 45 | 50 | 55 | 60 | 65 | 70 | 80 | 90 |
| Catalyst A | — | 78 | 82 | 86 | 89 | 92 | — | — | — |
| Catalyst B | — | 76 | 80 | 82 | 85 | 88 | 91 | — | — |
| Catalyst C | 66 | 82 | 86 (74) | 89 | 92 (83) | 95 | 96 (90) | 92 | 97 |
| Catalyst D | 59 | — | 68 | — | 72 | — | 81 | 94 | — |
| Catalyst E | 69 | — | 77 | — | 86 | — | 92 | 87 | — |

[a]—not tested; the values in parenthesis represent duplicate runs.

Table I shows that each of the invention catalysts (C, D, and E) had acetylene conversion at a given hydrogen conversion comparable to, or better than, the control catalysts A and B.

TABLE II

| | Ethane Selectivity[a] | | | | | | |
|---|---|---|---|---|---|---|---|
| Acetylene Conversion (%) | 55 | 65 | 75 | 80 | 85 | 90 | 95 |
| Catalyst A | — | — | — | 33 | 41 | 50 | — |
| Catalyst B | — | — | — | 35 | 50 | 65 | 90 |
| Catalyst C | 22 | 25 | 28 | 38 | 35 (33) | 41 | 50 (39) |
| Catalyst D | 40 | 45 | 53 | — | 33 | — | 70 |
| Catalyst E | 17 | 22 | 25 | — | 33 | — | 40 |

[a]See footnote [a], Table I.

Test data in Table II show that the invention catalysts C, D, and E consistently produced less undesirable product, ethane, than the two control catalysts A and B, at all acetylene conversion with the exception at 80% acetylene conversion. In other words, the invention catalysts had better selectivity to ethylene than the control catalysts.

EXAMPLE III

This example shows that the new catalyst composition, when used in a front end depropanizer selective hydrogenation process, lowers the oligomer formation in the product stream.

The catalysts were prepared as follows. Catalyst B was prepared as described in U.S. Pat. No. 5,587,348. It contained about 0.02 weight % Pd, 0.12 weight % Ag, and 0.3 weight % K (as KF) on 5/32" by 5/32" $\alpha$-Al$_2$O$_3$ pellets.

Catalyst G was a master batch of about 0.02 weight % Pd and 0.12 weight % Ag on $\alpha$-Al$_2$O$_3$, this catalyst was used in the preparation of catalysts H and I. The Pd/Ag/Al$_2$O$_3$ master batch (G) was prepared as follows: 100 g of $\alpha$-Al$_2$O$_3$ pellets UCI (United Catalyst Inc., 5/32" by 5/32") were soaked in 100 ml of an aqueous solution containing 0.02 g of Pd in the form of H$_2$PdCl$_4$ for 1 hour. The catalyst pellets were stirred several times over the hour to ensure an even distribution of Pd. At the end of the hour the clear solution was decanted off, the pellets were dried at 125° C. for 2 hours then calcined for 3 hours at 538° C. while purged with air.

Silver was then added by the method of incipient wetness. A solution of 0.189 g of AgNO$_3$ dissolved in 21 ml of distilled water was added to 100 g of the above-described Pd/Al$_2$O$_3$. The pellets were stirred to ensure even distribution of the Ag salt. The catalyst was then dried at 125° C. for 3 hours and calcined at 538° C. in air for 3 hours.

Catalyst H was prepared by adding 0.20 g of K$_2$SO$_4$ dissolved in 6.2 ml of distilled water to 30 g of G. This catalyst was then dried at 125° C. for 7 hours in an oven.

Catalyst I was prepared by adding 0.163 g of K$_3$PO$_4$ dissolved in 6.2 ml of distilled water to 30 g of G. This catalyst was then dried at 125° C. for 7 hours in an oven.

Catalyst J was the control catalyst, it was a commercial product sold by United Catalyst Inc. under the designation G83C. This catalyst contains 0.016 weight % Pd and 0.048 weight % Ag.

About 20 cc (23 g) of each of the above described catalysts was placed in a stainless steel reactor tube having a 0.5 inches inner diameter and a length of about 18 inches. The catalyst (resided in the middle of the reactor; both ends of the reactor were packed with 6 ml of 3 mm glass beads) was reduced at 38° C. for 1 hour under hydrogen at 12 l/hour at 200 psi. Thereafter, a hydrocarbon feed containing approximately (all by weight unless otherwise noted) hydrogen, 2.0%; methane, 22%; propylene, 23%; ethylene, 51%; acetylene, 5000 ppm; propadiene 5000 ppm; methylacetylene 5000 ppm; and carbon monoxide, 300 ppm (by volume) was continuously introduced into the reactor. The feed rate was 900 ml per minute at 200 psi. The reaction was allowed to run away, i.e., the uncontrollable hydrogenation of ethylene. During the runaway the heat of hydrogenation builds up such that the reactor temperature exceeds 250° F. The catalyst was then allowed to cool to room temperature, about 75° F. before data collection was started. The reactor temperature was gradually increased to the desired reaction temperature, the samples of the formed product were analyzed at various time intervals by means of a gas chromatograph. In the results shown in Table III, T1 is referred to as the cleanup temperature, that is the temperature at which the acetylene concentration falls below 20 ppm; T2 is referred to as runaway temperature, that is the temperature at which 3 weight % of ethylene is hydrogenated to ethane; $\Delta$T is the difference between T2 and T1. The $\Delta$T is a measure of ethylene selectivity which can also be viewed as a window of operability. Hydrocarbons containing 6 or more carbon atoms per molecule are referred to as heavies. Any hydrocarbon of 4 carbons is referred to as C$_4$.

TABLE III

| | | | | Hydrocarbon make at T1 | | | % remaining | |
|---|---|---|---|---|---|---|---|---|
| Catalyst | T1 | T2 | $\Delta$T | C$_2$[a] | C$_4$[a] | Heavies | MA[b] | PD[b] |
| B | 126 | 203 | 77 | 500 | 650 | 275 | 26.3 | 98.8 |
| H | 167 | 204 | 37 | 4,618 | 316 | 230 | 5.4 | 52.9 |
| I | 178 | 239 | 61 | 1,551 | 370 | 257 | 10.2 | 68.1 |
| J | 128 | 168 | 40 | 1,800 | 630 | 540 | 12.2 | 76.3 |

[a]C$_2$ denotes ethane;
C$_4$ denotes butanes, butenes and butadienes.
[b]MA= methylacetylene;
PD= propadiene.

The resulting in Table III show that the invention catalyst H and I had lower C$_4$ and heavies formations than either of the control catalysts, namely catalysts B and J.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed is:

1. A composition for use as a highly unsaturated hydrocarbon hydrogenation catalyst, said composition consists essentially of palladium, silver, an inorganic support, and a selectivity enhancer selected from the group consisting of phosphorus, phosphorus compounds, sulfur, sulfur compounds, and combinations of two or more thereof, wherein said palladium is present as skin on said supprt.

2. A composition according to claim 1 wherein said support is selected from the group consisting of spinel, alumina, silica, titania, zirconia, aluminosilicate, zinc aluminate, zinc titanate and combinations of two or more thereof.

3. A composition according to claim 1 wherein said inorganic support is alumina.

4. A composition according to claim 1 wherein selectivity enhancer is phosphorus.

5. A composition according to claim 1 wherein selectivity enhancer is sulfur.

6. A composition according to claim 1 wherein said selectivity enhancer is selected from the group consisting of potassium phosphate, sodium phosphate, ammonium phosphate, sodium sulfate, potassium sulfate, ammonium sulfate, and combinations of two or more thereof.

7. A composition according to claim 1 wherein said selectivity enhancer is potassium phosphate.

8. A composition according to claim 3 wherein said selectivity enhancer is potassium phosphate.

9. A composition according to claim 1 wherein said selectivity enhancer is potassium sulfate.

10. A composition according to claim 3 wherein said selectivity enhancer is potassium sulfate.

11. A composition for use as a highly unsaturated hydrocarbon hydrogenation catalyst, said composition consists essentially of palladium, silver, an inorganic support, and a selectivity enhancer, wherein said palladium is present as skin on said support and wherein said support is selected from the group consisting of spinel, alumina, silica, titania, zirconia, an aluminosilicate, and combinations of two or more thereof; and said selectivity enhancer is selected from the group consisting of potassium phosphate, sodium phosphate, ammonium phosphate, sodium sulfate, potassium sulfate, ammonium sulfate, and combinations of two or more thereof.

12. A composition according to claim 11 wherein said support is alumina; said selectivity enhancer is selected from the group consisting of potassium phosphate, potassium sulfate, and combinations thereof; and said palladium is present as skin on said support.

13. A composition for use as a highly unsaturated hydrocarbon hydrogenation catalyst, said composition consists essentially of palladium, silver, alumina, and a selectivity enhancer selected from the group consisting of potassium phosphate, potassium sulfate, and combinations thereof wherein said palladium is present as skin on said alumina.

* * * * *